(12) United States Patent
Grieshaber et al.

(10) Patent No.: US 6,332,866 B1
(45) Date of Patent: Dec. 25, 2001

(54) IRIS RETRACTOR FOR USE IN SURGICAL PROCEDURE ON THE EYE OF A LIVING BEING

(75) Inventors: Hans R. Grieshaber, Schaffhausen; Werner Maag, Glarus, both of (CH)

(73) Assignee: Grieshaber & Co. AG Schaffhausen, Schaffhausen (CH)

( * ) Notice: Subject to any disclaimer, the term of this patent is extended or adjusted under 35 U.S.C. 154(b) by 0 days.

(21) Appl. No.: 09/528,972

(22) Filed: Mar. 21, 2000

(51) Int. Cl.[7] ........................................ A61B 1/32
(52) U.S. Cl. ........................ 600/236; 600/210; 600/217
(58) Field of Search ................................... 600/236, 235, 600/210, 217, 202, 201

(56) References Cited

U.S. PATENT DOCUMENTS 3,840,015 * 10/1974 Gain .
3,935,640 * 2/1976 Cohan .
4,959,067 * 9/1990 Muller ................................. 606/190
5,556,417 * 9/1996 Sher ..................................... 600/236

* cited by examiner

Primary Examiner—Jeffrey A. Smith
(74) Attorney, Agent, or Firm—Henry M. Feiereisen

(57) ABSTRACT

An instrument for use in ophthalmic surgery, includes an elongated body portion having one end formed with an engagement member for insertion through an incision into the anterior chamber of the eye for retracting the iris. A fixation member is slidably secured to the body portion for positioning and fixing the body portion in place. The body portion is made of a flexible polymeric material having a hue which contrasts a hue of the iris, at least along an area starting from the engagement member to at least half the length of the body portion.

23 Claims, 2 Drawing Sheets

FIG. 4
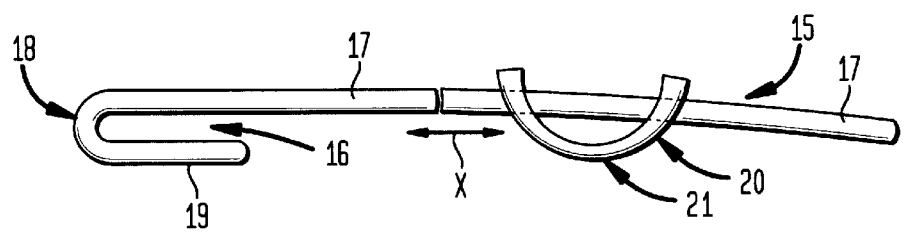
FIG. 5
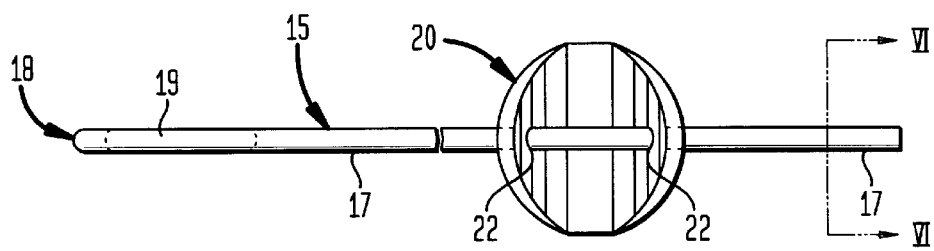
FIG. 6     FIG. 6A     FIG. 9
  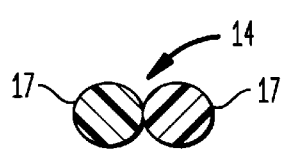
FIG. 7
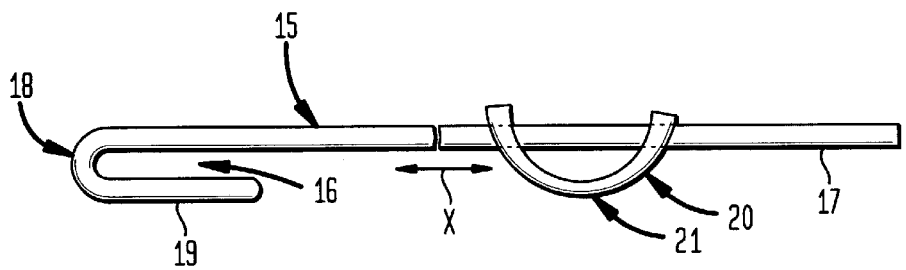
FIG. 8
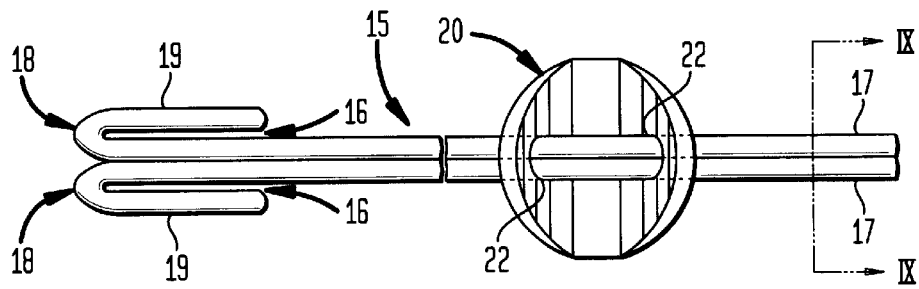

IRIS RETRACTOR FOR USE IN SURGICAL PROCEDURE ON THE EYE OF A LIVING BEING

BACKGROUND OF THE INVENTION

The present invention generally refers to a surgical instrument for use in ophthalmic surgery, and in particular to an iris retractor for use in eye surgery of a living being for retraction of the iris.

Iris retractors are known which generally include an elongated body portion with a substantially hook-shaped end for retracting the iris, and a fixation member slidably mounted on the body portion for securing the iris retractor in place when the body portion is inserted with its hook-shaped end into the anterior chamber through a suitable incision made in the cornea.

It is well known that adequate dilatation of the pupil of the eye is essential during e.g. cataract surgery. In particular, for removal of a cataract, the surgical procedure in the posterior section as well as anterior section of the eye requires a sufficiently large and constant viewing range for the surgeon. Generally, the dilatation of the pupil is effected through administration of pharmaceuticals. However, on occasions, the use of pharmaceuticals is insufficient to attain the desired dilatation so that the use of surgical instruments for retracting the iris is proposed, e.g. application of one or more suitably spaced iris retractors which attach to the iris to pull it outwardly for enlarging the opening of the pupil. The individual iris retractors are inserted into the anterior chamber of the eye through an incision in the cornea and suitably fixed in tight manner by the fixation member at the outer contour of the eye. After surgery, the iris retractor is released from the iris and withdrawn from the anterior chamber of the eye.

European Pat. No. 0 653 197 describes an iris retractor for use in the ophthalmic surgery, with the iris retractor having a body portion formed at one end with a hook-shaped engagement member for insertion into the anterior chamber of the eye and withdrawal of the iris. A plate-shaped fixation member is slidably mounted to the body portion to hold the body portion in place in the region of the transition area from the cornea to the sclera.

U.S. Pat. No. 5,716,328 describes an iris retractor which includes an elongated body portion for insertion through an incision in the eye to retract the iris, with the body portion including two parallel shafts secured to each other along a common longitudinal edge wherein each shaft has at least one end formed with a hook-shaped member. The shafts of the body portion are so joined together that the hook-shaped members diverge from the longitudinal edge downward at an angle to one another to exhibit a Λ-shaped configuration, and exhibit parallel shanks which are spaced from each other at a distance, the dimension of which depends on the angle between the hook-shaped members.

In both these conventional iris retractors, the individual body portion has a length of about 5 mm to 8 mm and is made of a flexible polymeric material with a diameter of about 0.15 mm to 0.20 mm, whereas the hook-shaped engagement member has a length of about 1.0 mm to 1.5 mm.

The use of such iris retractors for ophthalmic surgery in the anterior or posterior eye sections suffers, however, shortcomings as far as recognition is concerned. As a result of their relatively small size, the surgeon has oftentimes great difficulty to see the individual iris retractors during the process of inserting the retractors into the anterior chamber and attaching the retractors to the iris or removing them from the eye. This may potentially adversely affect the surgery.

SUMMARY OF THE INVENTION

It is thus an object of the present invention to provide an improved iris retractor, obviating the afore-stated drawbacks.

In particular, it is an object of the present invention to provide an improved iris retractor which is easily recognizable during surgical procedure and subsequent withdrawal so as to enable the surgeon to clearly and reliably determine the disposition of the iris retractor.

These objects, and others which will become apparent hereinafter, are attained in accordance with the present invention by providing an elongated body portion having one end formed with an engagement member for insertion through an incision into the anterior chamber of the eye for retracting the iris, and a fixation member slidably secured to the body portion for positioning and fixing the body portion in place, wherein the body portion is made of a flexible polymeric material having a hue which contrasts a hue of the iris, at least along an area starting from the engagement member to at least half the length of the body portion.

Through the provision of an iris retractor according to the present invention, the surgeon can easily ascertain the individual iris retractors when inserted in the eye and spaced around the iris, and can reliably withdraw the single iris retractors from the eye after surgery. Thus, the position of an iris retractor can be visually established without any problems, essentially eliminating the risk that the iris retractor inadvertently contacts the iris or other parts of the eye during the process of introducing or removing the retractors into or from the eye.

According to another feature of the present invention, the body portion may be made of a flexible polymeric filament of circular or elliptic cross section, having a homogenous hue which contrasts the hue of the iris. Suitably, the body portion may have a cross section which is colored homogenously in red, glaring red, brown, black, deep black, yellow and white.

According to another feature of the present invention, the fixation member may be made of a caoutchouc mixture, e.g. a silicone caoutchouc mass, which exhibits a glaring and visually distinct hue.

BRIEF DESCRIPTION OF THE DRAWING

The above and other objects, features and advantages of the present invention will be more readily apparent upon reading the following description of a preferred exemplified embodiment of the invention with reference to the accompanying drawing, in which:

FIG. 4 is an enlarged side view of the iris retractor of FIG. 2, comprised of body portion and fixation member;

FIG. 5 is a top view of the iris retractor of FIG. 4;

FIG. 6 is a cross sectional view of the body portion of the iris retractor, taken along the line VI—VI in FIG. 5;

FIG. 6A is a cross sectional view of a modified body portion of the iris retractor of FIG. 2;

FIG. 7 is an enlarged side view of the iris retractor of FIG. 3, comprised of body portion and fixation member;

FIG. 8 is a top view of the iris retractor of FIG. 7; and

FIG. 9 is a cross sectional view of the body portion of the iris retractor, taken along the line IX—IX in FIG. 8.

DETAILED DESCRIPTION OF PREFERRED EMBODIMENTS

Figure 1:
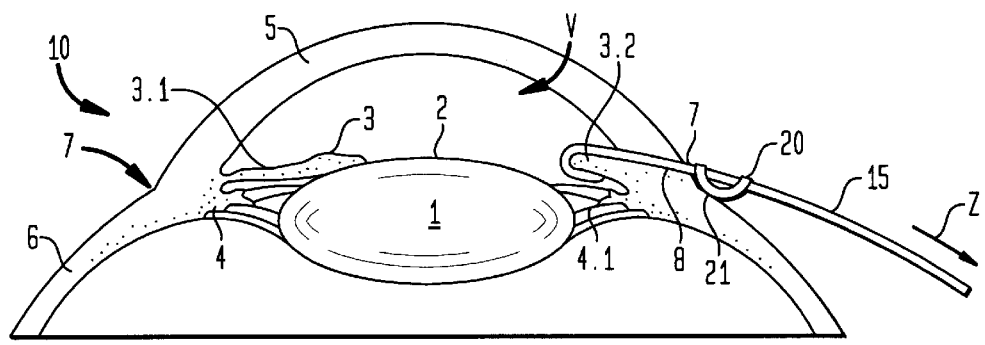
FIG. 1 is an enlarged schematic illustration of the forward eye section of a living being, illustrating one region of the iris being retracted by an iris retractor according to the present invention.

Throughout all the Figures, same or corresponding elements are generally indicated by same reference numerals.

Turning now to the drawing, and in particular to FIG. 1, there is shown an enlarged schematic illustration of the forward eye section of a living being, generally designated by reference numeral 10 and including the anterior chamber, designated in its entirety by reference character V, the lens 1 (ocular) with the ciliary bodies 4 and zonule fibers 4.1, the pupil 2, the iris generally designated by reference numeral 3 and including both circular areas 3.1 and 3.2, the cornea 5, and the sclera 6. For a surgical procedure in the anterior eye section as well as in the posterior eye section, the provision of a greatest possible and constant viewing field for the surgeon (ophthalmologist) is a prerequisite for a successful procedure. To accomplish a desired viewing field, an iris retractor, generally designated by reference numeral 15 is inserted in a first phase into the anterior chamber V through an incision 8 in a transition 7 between the cornea 5 and the sclera 6. After engaging behind the circular area 3.2 of the iris 3, the circular area 3.2 is pulled outwards in the direction of arrow Z. The iris retractor 15 is held in proper position at the transition 7 by a fixation member 20 which is mounted on the iris retractor 15 for displacement in longitudinal direction. The fixation member 20 is suitably elastically deformable and provided with an arcuate seat surface 21 to substantially conform to the transition 7.

Figure 2:
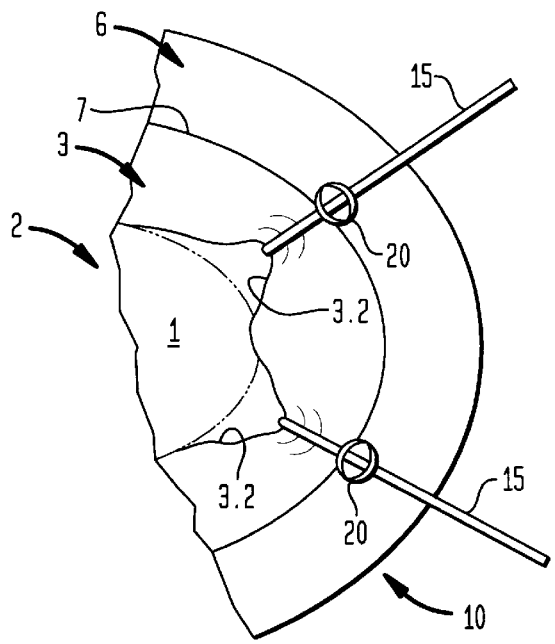
FIG. 2 is an enlarged, schematic plan view of a portion of the eye, showing by way of example a partial retraction of the iris at two locations by means of a first type of iris retractor.

FIG. 2 shows an enlarged, schematic plan view of a portion of the eye, showing by way of example a partial retraction of the iris 3 by two iris retractors 15 which are held in proper position by the fixation members 20 at the transition 7 between the cornea 5 and the sclera 6. The configuration of the iris retractor 15 is shown in more detail in FIGS. 4 and 5, with FIG. 4 depicting a side view of the iris retractor 15, and with FIG. 5 depicting a top view thereof. The iris retractor 15 includes a body portion in the form of an elongate, slightly curved, shaft 17 having one end which is bent over once in a hairpin-like manner to provide a hook-shaped engagement member 18 having a shank 19 in parallel relation to the shaft 17 at formation of a gap 16. The fixation member 20, mounted on the shaft 17 for displacement in direction of double arrow X is configured, for example, as a circular disk having two spaced-apart bores 22 for passage of the shaft 17. The bores 22 are so arranged relative to one another that the flexible fixation member 20 can be shifted along the shaft 17, when squeezed together, and is held in place at a desired location, when releasing the fixation member 20, whereby the arcuate seat surface 21, formed by the fixation member 20, rests at the transition 7 of the eye 10 with the iris 3 being retracted in a manner shown in FIG. 1. As shown in FIG. 6, the shaft 17 may have a circular cross section, or, as shown in FIG. 6A, an elliptic cross section.

Figure 3:
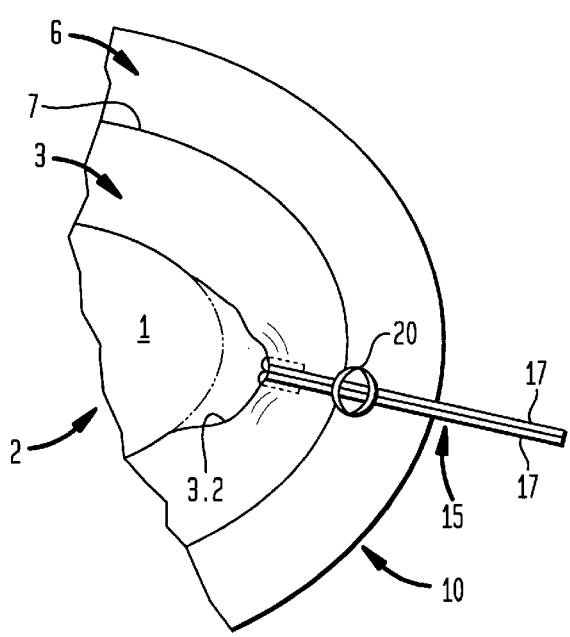
FIG. 3 is an enlarged, schematic plan view of a portion of the eye, showing by way of example a partial retraction of the iris at a random location by means of a second type of iris retractor.

Turning now to FIG. 3, there is shown another type of iris retractor 15 for partial retraction of the iris 3, which differs from the iris retractor of FIG. 4 in that the body portion is comprised of two substantially elongated shafts 17 which extend parallel to one another and are suitably joined together, e.g. by an adhesive, along a longitudinal edge 14, as shown in FIG. 9. The shafts 17 have a generally circular cross section and terminate in engagement members 18 which exhibit a hook-shaped configuration, by bending over once the ends of the shafts 17, and have shanks 19 which extends parallel to the shafts 17 at a distance 16, as shown in particular in FIGS. 7 and 8. The hook-shaped engagement members 18 are arranged at an acute angle to one another to exhibit a downwardly diverging substantially Λ-shaped configuration. A fixation member, such as fixation member 20, is slipped over both shafts 17 for displacement in direction of double arrow X and is formed as circular disk with two spaced-apart bores 22 for allowing displacement of the fixation member 20 in longitudinal direction and securement of the fixation member 20 at a desired location.

In order to provide a surgeon, operating on the eye 10, a tool to unmistakably see each iris retractor 15 during the surgical procedure, the body portion of the iris retractor 15 is made, at least from an area extending axially from the hook-shaped engagement members 18 to half the entire length of the body portion, preferably however over the entire length of the body portion, of a flexible polymeric material which has a hue that clearly contrasts the hue of the iris 3 at hand. A preferred example for the polymeric material includes a polyamide filament. According to another variation, the flexible polymeric material or polyamide filament may be provided in axial direction with an outer, circular ring shaped envelope of particles which has a color whose hue contrasts the color of the iris 3. It is also within the scope of the present invention, to provide the flexible polymeric material or polyamide filament with a cross section that is homogenously colored in contrast to the hue of the iris 3.

Also the fixation member 20 is suitably made of a caoutchouc mixture, e.g. silicone caoutchouc mass, exhibiting a glaring and visually distinct color.

Suitably, the body portion and the fixation element 20 of the iris retractor 15 has a flat, dull outer surface to avoid an undesired reflection. In the following, examples for the colored iris retractor 15 are provided in dependence to the hue of the iris 3 of the eye 10:

a) For a hue of the iris 3 of: blue, bluish gray, green, green gray or a blend thereof, the color of the body portion should be: red, glaring red, brown, black or deep black.

b) For a hue of the iris 3 of: brown or dark mixed color, the color of the body portion should be: yellow or white.

It will be understood by persons skilled in the art that the above examples should not be considered exhaustive so that the present invention should not be limited thereto as other combinations are conceivable as well and thus within the scope of the present invention, so long as the iris retractor 15 is clearly and visibly contrasted from its background, i.e. from the hue of the iris 3. For example, appropriate mixed colors of the flexible polymeric material for the body portion as well as for the fixation member 20 of caoutchouc mixture should be covered by the present invention.

While the invention has been illustrated and described as embodied in a iris retractor for use in surgical procedure on the eye of a living being, it is not intended to be limited to the details shown since various modifications and structural changes may be made without departing in any way from the spirit of the present invention.

What is claimed as new and desired to be protected by Letters Patent is set forth in the appended claims:

1. An instrument for use in ophthalmic surgery, comprising an elongated body portion having one end formed with an engagement member for insertion into the anterior chamber of the eye for retracting the iris, said body portion being defined by a length; and a fixation member slidably secured to the body portion for positioning and fixing the body portion in place;

said body portion being made of a flexible polymeric material having a hue at least along an area starting from the engagement member to at least half the length of the body portion, said hue of the body portion being selected to contrast a hue of the iris of a patient and from a plurality of hues which contrasts a plurality of iris hues from a plurality of patients.

2. The instrument of claim 1 wherein the body portion is made over its entire length of a flexible polymeric material having an optical warning color.

3. The instrument of claim 1 wherein the body portion is made over its entire length of a flexible polymeric material having a cross section of a homogenous and contrasting color.

4. The instrument of claim 1 wherein the body portion is made at least along said area of a flexible polymeric filament having a circular cross section and exhibiting a homogenous hue which contrasts the hue of the iris.

5. The instrument of claim 1 wherein the body portion is made at least along said area of a flexible polymeric filament having an elliptic cross section and exhibiting a homogenous hue which contrasts the hue of the iris.

6. The instrument of claim 1 wherein the body portion has a cross section which is colored homogenously at least along said area in a hue selected from the group consisting of red, glaring red, brown, black, deep black, yellow and white.

7. The instrument of claim 6 wherein the body portion is made of a polyamide filament.

8. The instrument of claim 1 wherein the body portion has an outer envelope of particles oriented in axial direction of the body portion and defined by a circular cross section, said envelope of particles being so colored as to contrast the hue of the iris.

9. The instrument of claim 8 wherein the envelope of particles is colored in a hue selected from the group consisting of red, glaring red, brown, black, deep black, yellow and white.

10. The instrument of claim 8 wherein the envelope of particles is colored homogenously in a hue selected from the group consisting of red, brown and yellow.

11. The instrument of claim 1 wherein the fixation member is made of a caoutchouc mixture of a visually distinct glaring color.

12. The instrument of claim 11 wherein the caoutchouc mixture is a silicone caoutchouc mass.

13. The iris retractor of claim 1 wherein the engagement member is hook-shaped.

14. An instrument for use in ophthalmic surgery, comprising an elongated body portion having one end formed with an engagement member for insertion into the anterior chamber of the eye for retracting the iris; and a fixation member slideably secured to the body portion for positioning and fixing the body portion in place, wherein at least the body portion is made of a flexible polymeric material having a hue which is selected to contrast a hue of the iris of a patient and selected from a plurality of hues to contrast iris hues from different patients.

15. The instrument of claim 14 having two said body portion, each said body portion being made of a flexible polymeric material having a hue which contrasts a hue of the iris.

16. The instrument of claim 14 wherein the body portion is colored in red or glaring red for use with an iris having blue, bluish gray, green, green gray hue or a mixture thereof.

17. The instrument of claim 14 wherein the body portion is colored in brown, black or deep black for use with an iris of blue, bluish gray, green, green gray hue or a mixture thereof.

18. The instrument of claim 14 wherein the body portion is colored in yellow or white for use with an iris of brown or a dark mixed color.

19. A kit, comprising a plurality of iris retractors made of flexible polymeric material, wherein the iris retractors have different hues and are selected so as to contrast a hue of the iris of a patient during a surgical procedure on the eye.

20. The kit of claim 19 wherein the flexible polymeric material is a polyamide filament.

21. The kit of claim 19 wherein the iris retractors have a circular or elliptic configuration.

22. The iris retractor of claim 21 wherein the caoutchouc mixture is a silicone caoutchouc mass.

23. The kit of claim 19 wherein each of the iris retractors has a fixation member for securing the iris retractor in place, said fixation member made of a caoutchouc mixture having a visibly distinct and glaring color.

* * * * *